United States Patent [19]

Passaniti et al.

[11] Patent Number: 5,382,514
[45] Date of Patent: Jan. 17, 1995

[54] IN VIVO ANGIOGENESIS ASSAY

[75] Inventors: Antonino Passaniti, Baltimore; George R. Martin, Bethesda, both of Md.

[73] Assignee: The United States of America as represented by the Secretary of the Department of Health and Human Services, Washington, D.C.

[21] Appl. No.: 862,622

[22] Filed: Mar. 31, 1992

[51] Int. Cl.⁶ .................. G01N 33/567; G01N 33/574
[52] U.S. Cl. .................................. 435/7.21; 435/7.23; 435/29; 436/63; 436/64; 436/813; 424/9; 424/520; 424/572
[58] Field of Search ................. 435/7.23, 7.21, 29; 436/63, 64, 813; 424/9, 85.1, 520, 572

[56] References Cited

U.S. PATENT DOCUMENTS 5,158,874  10/1992  Kleinman et al. .................. 435/34

OTHER PUBLICATIONS

Sweeney, T. M., et al., Cancer Metastasis Rev., vol. 10, No. 3, pp. 245–254 (1991) Abstract Only.
Murata, et al., Cancer Res., vol. 51, No. 1, pp. 22–26, 1991.
Passaniti, et al., Lab. Invest., vol. 67, No. 4, pp. 519–528, 1992.
Kleinman et al., "Basement Membrane Complexes with Biological Activity", *Biochemistry*, vol. 25 (1986), pp. 312–318.
Drabkin et al., "I. Spectrophotometric Constants for Common Hemoglobin Derivatives in Human, Dog, and Rabbit Blood", *J. Biol. Chem.*, vol. 98 (1932), pp. 719–733.
Bradford, "A Rapid and Sensitive Method for the Quantitation of Microgram Quantities of Protein Utilizing the Principle of Protein–Dye Binding", *Analytical Biochemistry*, vol. 72 (1976), pp. 248–254.
Auerbach et al., "Regional Differences in the Incidence and Growth of Mouse Tumors Following Intradermal of Subcutaneous Inoculation", *Cancer Research*, vol. 38 (1978), pp. 1739–1744.
Cartun et al., "An Immunocytochemical Technique Offering Increased Sensitivity and Lowered Cost with a Streptavidin–Horseradish Peroxidase Conjugate", *The Journal of Histotechnology*, vol. 12, No. 4 (1989), pp. 273–277.

*Primary Examiner*—Toni R. Scheiner
*Attorney, Agent, or Firm*—Lowe, Price, LeBlanc & Becker

[57] ABSTRACT

A method of performing in vivo angiogenesis assays which involves the use of a matrix material which can be maintained in an injectable solution form at a temperature below that of a host and which forms a gel matrix when injected into a host. The matrix material is an extract of murine basement membrane. Angiogenic factors, including inducers and inhibitors can be added to the matrix material prior to injection into a host. After a period of time within the host, the gel matrix is recovered and angiogenesis of the recovered matrix gel is quantitated. The procedure can be used to induce vascularization or inhibit vascularization at a tissue situs as desired.

10 Claims, 8 Drawing Sheets

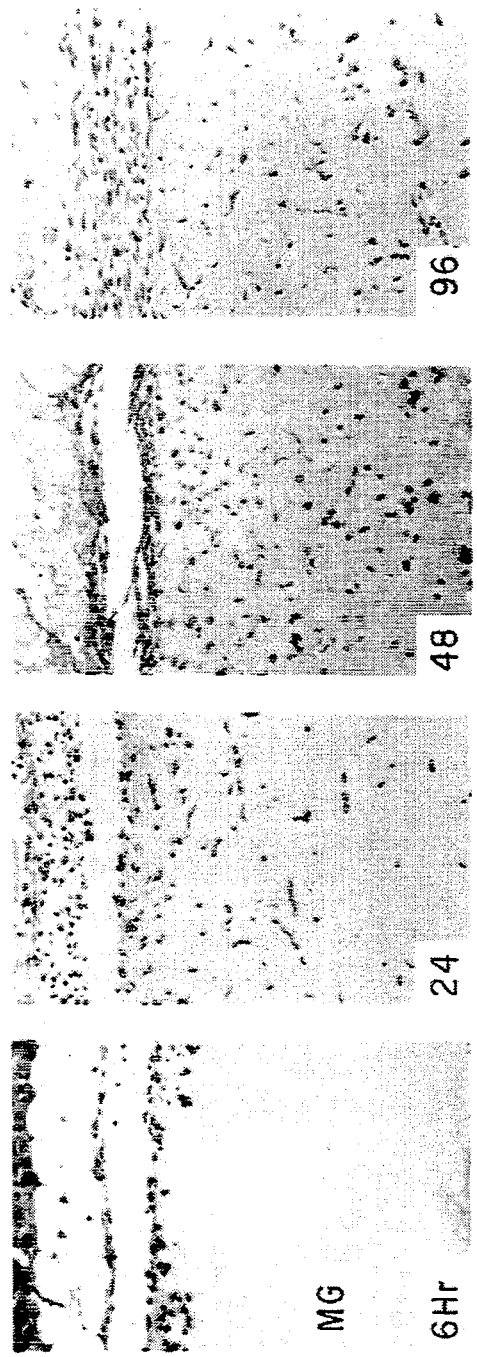

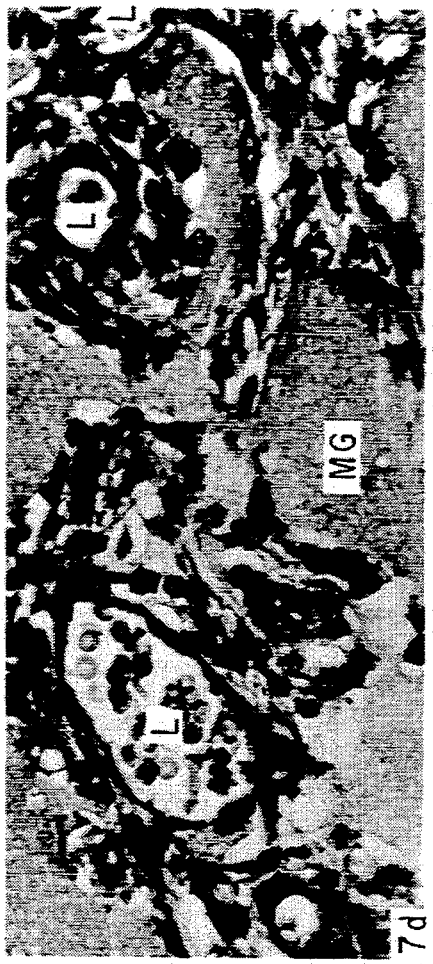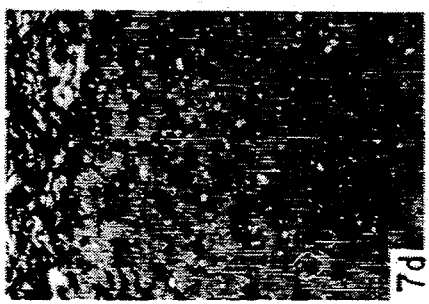
FIG. 4F
FIG. 4G
FIG. 4E

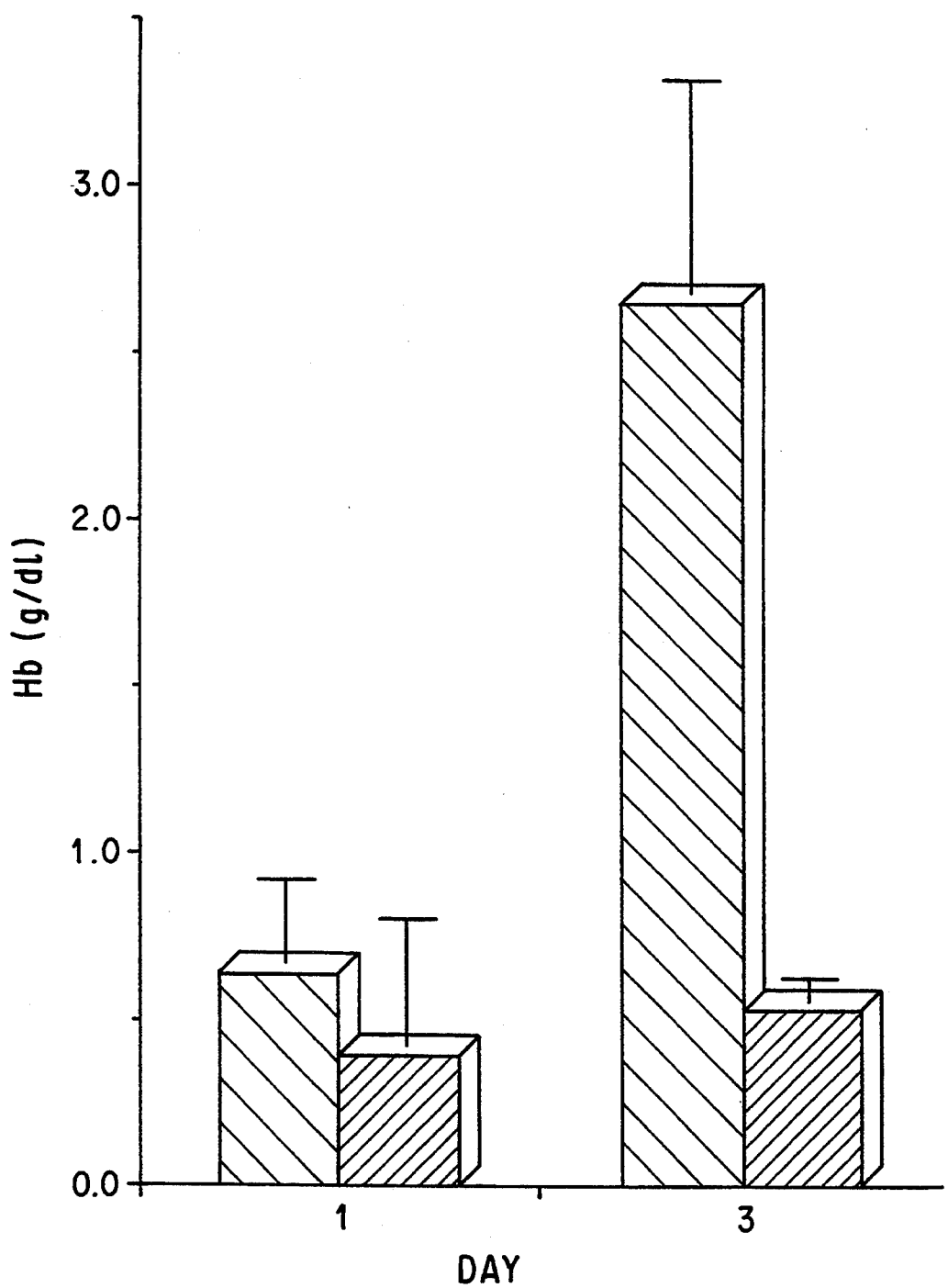
F I G. 7

IN VIVO ANGIOGENESIS ASSAY

TECHNICAL FIELD

The present invention relates to a method of performing in vivo angiogenesis assays. More specifically, the present invention relates to a simple, rapid, and quantitative assay to assess inducers as well as inhibitors of angiogenesis.

In addition, the present invention relates to a method of inducing a rapid and reproducible formation of new blood vessels which has the potential to increase the blood flow to any given tissue site and which also allows the detection of factors which promote or inhibit vascularization.

BACKGROUND ART

Neovascularization, vasculogenesis, and angiogenesis are terms which describe the process whereby new capillaries are formed.

The development of a vascular supply is essential for the growth, maturation, and maintenance of normal tissues. It is also required for wound healing and the rapid growth of solid tumors and is involved in a variety of other pathological conditions. Current concepts of angiogenesis, based in large part on studies on the vascularization of tumors, suggest that cells secrete angiogenic factors which induce endothelial cell migration, proliferation, and capillary formation. While the factors that induce angiogenesis in situ are not well identified, numerous factors have been identified which induce vessel formation in vitro or in vivo in animal models. These include: aFGF, bFGF, TGF-α, TNF-α, VPF, or VEGF, monobutyrin, angiotropin, angiogenin, hyaluronic acid degradation products, and AGE-products. Also, many compounds have been described as inhibitors of angiogenesis including a cartilage-derived inhibitor, identified as TIMP, PF-4, thrombospondin, laminin peptides, heparin/cortisone, minocycline, fumagillin, difluoromethyl ornithine, and sulfated chitin derivatives.

The major development of the vascular supply occurs during embryonic development, at ovulation during formation of the corpus luteum, and during wound and fracture healing. However, many pathological disease states are characterized by augmented angiogenesis including tumor growth, diabetic retinopathy, neovascular glaucoma, psoriasis, and rheumatoid arthritis among other conditions. During these processes normally quiescent endothelial cells which line the blood vessels sprout from sites along the vessel, degrade extracellular matrix barriers, proliferate, and migrate to form new vessels. These processes are believed to be induced by factors secreted by the tissues to be vascularized and are often referred to as angiogenic factors. Angiogenic factors are secreted from surrounding tissue during the process which directs the endothelial cells to degrade stromal collagens, undergo directed migration (chemotaxis), proliferate, and reorganize into capillaries.

Several models for including angiogenesis in vivo have been developed. The corneal pocket assay involves the surgical implantation of polymer pellets containing angiogenic factors in the cornea of larger animals such as rabbits. Quantitation is difficult and the number of tests conducted is limited. The chick chorioallantoic membrane (CAM) assay involves the removal and transfer of a chick embryo from the shell to a cup. The angiogenic material is dried on a glass cover slip and placed on the chorioallantoic membrane and the appearance of new vessels is observed. The rabbit ear chamber assay requires the surgical insertion of a glass or plastic viewing device and measurement of capillary migration by microscopy. However, it is difficult to apply angiogenic materials in this assay. The rat dorsal air sac assay involves implants of stainless steel chambers containing angiogenic factors and is difficult to quantiate. An alginate assay which generates an angiogenic response has been described which involves the injection of tumor cells encased in alginate subcutaneously into mice. The accumulation of hemoglobin in the injected gel is used to quantitate the angiogenic response.

While each of these assays have many uses, some suffer from several major disadvantages which make their application to the development of anti-angiogenic agents difficult and cumbersome. First, some of these assays are not readily quantitated. The responses observed are often graded as positive and negative which results in poor reproducibility. Secondly, agents must be embedded in controlled release polymers, a process which may lead to inactivation of many biological activators or inhibitors of angiogenesis. Finally, the assays are cumbersome because they either employ larger, expensive animals or because the application of the test substances is tedious. Several in vitro assays of endothelial cell growth, migration, and capillary tube formation while useful in unlocking specific mechanisms in the angiogenic process are, of course, only initial screening methods for angiogenic or angiostatic substances. The final test must employ in vivo animal testing.

DISCLOSURE OF THE INVENTION

It is one object of the present invention to provide a method of performing angiogenesis assays.

Another object of the present invention is to provide a method of performing in vivo angiogenesis assays.

A further object of the present invention is to provide a method of quantitively assaying inducers of angiogenesis.

A further object of the present invention is to provide a method of quantitively assaying inhibitors of angiogenesis.

A still further object of the present invention is to provide a method of inducing vascularization at a tissue situs.

A still further object of the present invention is to provide a method of inhibiting vascularization at a tissue situs.

According to these and further objects of the invention which will become apparent as the description thereof is presented below, the present invention provides for a method of performing an in vivo angiogenesis assay which involves:

providing a liquid matrix material which forms a matrix gel when injected into a host;
    adding an angiogenic agent to the liquid matrix material;
    injecting the liquid matrix material containing the angiogenic agent into a host to form a matrix gel;
    recovering the matrix gel from the host; and
    quantitating angiogenesis of the recovered matrix gel The present invention also provides for a method of inducing vascularization in a tissue situs which involves:

providing a liquid matrix material which forms a matrix gel when injected into a host;

adding an angiogenic inducing agent to the liquid matrix material; and injecting the liquid matrix material containing the angiogenic inducing agent into a tissue situs of a host to form a matrix gel.

In addition, the present invention provides for a method of inhibiting vascularization in a tissue situs which comprises:

providing a liquid matrix material which forms a matrix gel when injected into a host;

adding an angiogenic inhibiting agent to the liquid matrix material; and injecting the liquid matrix material containing the angiogenic inhibiting agent into a tissue situs of a host to form a matrix gel.

BRIEF DESCRIPTION OF DRAWINGS

The present invention will be described with reference to the attached drawings which are given by way of non-limiting examples only, in which:

FIG. 4A-4G are the histological analysis of recovered gels showing time course of vessel formation.

FIG. 6A shows the mean area over 8 days for vWF. FIG. 6B shows the Hemoglobin content over 8 days.

FIG. 7 is a bar graph showing inhibition by TIMP.

BEST MODE FOR CARRYING OUT THE INVENTION

Figure 1:
FIG. 1A is a photograph of MATRIGEL gels on day 4 after subcutaneous injection in a mouse.
FIG. 1B is a photograph of MATRIGEL supplemented with 1 ng/ml FGF and 40 U/ml heparin on day 1 after subcutaneous injection in a mouse.
FIG. 1C is a photograph of MATRIGEL supplemented with 1 ng/ml FGF and 40 U/ml heparin on day 4 after subcutaneous injection in a mouse.

The present invention involves a simple, rapid, and quantitative method to assay inducers as well as inhibitors of angiogenesis. According to the present invention, a solution of basement membrane proteins supplemented with fibroblast growth factor and heparin is injected subcutaneously in a host, e.g., a mouse, where it forms a gel. Sprouts from vessels in the adjacent tissue penetrate into the gel within days connecting it with the external vasculature. Angiogenesis is then quantitated by image analysis of vessels and by measuring the hemoglobin present in the vessels within the gel. This assay method facilitates the testing of both angiogenic and angiostatic agents in vivo. In addition, the endothelial cells responding to the angiogenic factors can be recovered in vitro for further studies.

According to the present invention liquid MATRIGEL maintained at 4° C. is used as a vehicle to inject angiogenic factors subcutaneously into a host, e.g., mice. Various components may be mixed with liquid MATRIGEL at 4° C. which, when injected into a host, form a single, readily recovered gel. Such gels may be removed at various times and processed for histology, total protein, and hemoglobin content.

The angiogenic factors and vehicle were prepared according to the present invention in the following manner. MATRIGEL, an extract of murine basement membrane proteins, consisting predominantly of laminin, collagen IV, heparin sulfate proteoglycan, and nidogen and entactin was prepared from the EHS tumor as described Kleinman et al, "Basement Membrane Complexes with Biological Activity", *Biochemistry*, Vol. 25 (1986), pages 312–318, the disclosure of which is expressly incorporated herein by reference, sterilized by dialysis against chloroform, and stored at −20° C. Before use. MATRIGEL was thawed at 4° C. and placed immediately on ice prior to the addition of aFGF, heparin, or other growth factors.

Heparin was dissolved in sterile phosphate buffered saline (PBS) to a concentration of 16,000 U/ml. Further dilutions were made with sterile filtered PBS containing 1 mg bovine serum albumin (BSA)/ml. Acidic fibroblast growth factor (aFGF;HBGF-1) (obtained from R & D Inc.) was diluted to 0.25 μg/ml with PBS/BSA. Various amounts of heparin and/or FGF were mixed with 0.5–1.0 ml of Matrigel at 4° C. in proportions not exceeding 1% of the volume of Matrigel to be injected. In some cases, other factors were included as noted.

Features and characteristics of the present invention will be described with reference to the following examples which are given for illustrative purposes only.

EXAMPLE 1

In this example, C57BL mice (Jackson Laboratories, Bar Harbor, Me.; 5 per data point) were each injected subcutaneously with 0.5 ml of Matrigel and 0–100 ng aGFG/ml and 0–64 U heparin/ml near the abdominal midline using a 25 gauge needle. The injected MATRIGEL rapidly formed a single, solid gel which persisted for at least 10 days in the mice. Mice were subsequently sacrificed and the gels were recovered and processed for further studies. Typically, the overlying skin was removed and the gels were cut out by retaining the peritoneal lining for support. For most histological sections, the skin and underlying peritoneum were formalin-fixed immediately after dissection.

Hemoglobin was measured using the Drabkin method Drabkin et al, "I Spectrophotometric Constants for Common Hemoglobin Derivatives in Human, Dog, and Rabbit Blood", *J. Biol. Chem.*, Vol. 98 (1932), page 719, the disclosure of which is expressly incorporated herein by reference, and Drabkin reagent kit #525 (Sigma). Briefly, gels were dispersed with 500 μl of dH₂O and incubated overnight at 37° C. with shaking to lyse RBC. Tissue was crushed with a syringe barrel, the liquid was removed, and centrifuged to remove cells. Supernatant (50 μl) was mixed with 1.0 ml of Drabkin reagent (bicarbonate, ferricyanide, cyanide), vortexed, incubated for 90 min at 24° C. and the absorbance of cyanomethemoglobin was determined spectrophotometrically at 540 nm. Samples for each point were from 5 different mice. The concentration of hemoglobin was calculated using a standard curve obtained from a known amount of hemoglobin assayed in parallel. Protein content of the supernatant fluid was determined using the BioRad protein assay method described in Bradform, "A Rapid and Sensitive Method for the Quantitation of Microgram Quantities of Protein Utilizing the Principle of Protein Dye Binding", *Anal. Biochem.*, Vol. 72 (1972), pages 248–254, the disclosure of which is expressly incorporated herein by reference. The Optomax image analysis system (Optomax, Hollis N.H.) was used for quantitation of histological specimens by light microscopy.

In developing a more reproducible and quantitative angiogenic model, fibroblast growth factors which are proven and potent inducers of neovascularization were utilized. When injected alone subcutaneously into mice, neither aFGF nor bFGF induced any visible signs of neovessel formation (data not shown). This is not unexpected since the factors would be expected to be rapidly cleared from the site. MATRIGEL, a solution of basement membrane proteins isolated from the EHS tumor was tested, as a vehicle for the slow release of angiogenic factors since it is a liquid at 4° C. but forms a gel in vivo.

FIG. 1A is a photograph of Matrigel gels on day 4. FIG. 1B is a photograph of MATRIGEL supplemented with 1 ng/ml FGF and 40 U/ml heparin on day 1. FIG. 1C is a photograph of Matrigel after subcutaneous injection. In FIGS. 1A–1C the overlying skin was removed exposing the gels. Note that the surface of the gels as well as the overlying skin flaps contain many vessels. The bleeding seen here was also seen with some MATRIGEL/FGF and Matrigel/heparin injections but these produced little or no vessel infiltration and accounted for less than 10% of the amount of hemoglobin found in MATRIGEL/FGF/heparin gels at 4 days (see also Table 1). Indeed, the present studies showed that the gels which formed following the subcutaneous injection of matrigel alone were readily distinguished from surrounding tissue, persisted for at least 10 days, and produced little or no local reaction or angiogenic response (FIG. 1A).

MATRIGEL supplemented with FGF alone produced gels which showed a variable angiogenic reaction (data not shown). The magnitude of the angiogenic response was considerably greater in gels supplemented with both FGF and heparin (FIGS. 1B, 1C). Injection of MATRIGEL plus aFGF and heparin at the ventral midline achieved optimal and reproducible responses while material injected either anteriorly or posteriorly to the midline resulted in less consistent responses. Auerbach et al, "Regional Differences in the Incident and Growth of Mouse Tumors Following Intradermal or Subcutaneous Inoculation", *Cancer Res.* 38:1739–1744, 1978, found similar regional differences in tumor growth which might also be related to the capacity for vascularization at these sites. Dorsal injections also induced consistent responses, but the abdominal location was used almost exclusively in this study.

Figure 2:
FIG. 2 is a photograph of MATRIGEL recovered after 4 days in vivo showing angiogenic response as a function of heparin concentration.

FIG. 2 is a photograph of MATRIGEL recovered after 4 days in vivo showing angiogenic response as a function of heparin concentration. Mice were injected with MATRIGEL and aFGF as in FIG. 1C but with various heparin doses. After sacrificing the animals, the skin was removed and the gels were cut out with intact peritoneal lining for support and placed on tissue culture dishes for photography. Each gel was between 0.8 and 1.4 cm in length. The heparin dependence of the response is apparent (see also Table 1). The tissue in contact with the FGF- and heparin-supplemented gels contained abundant and readily visible blood vessels as seen from FIG. 2.

Figure 3A:
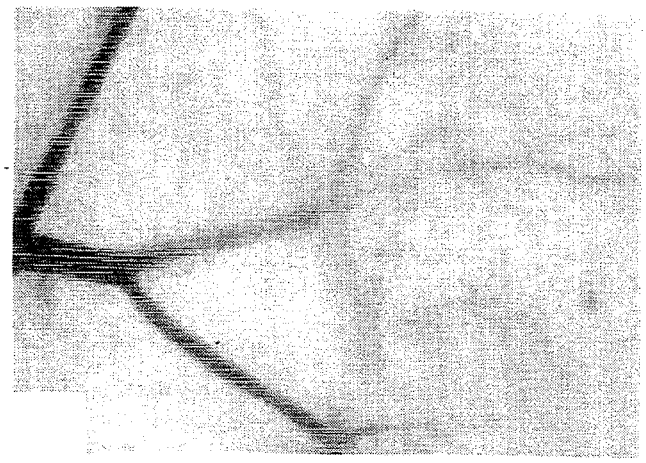
FIGS. 3A, 3B and 3C are photographs of vessels associated with the FGF/heparin-supplemented gels. Vessels surrounding the gel appear to derive from the skin and peritoneal linings (FIGS. 3A and 3B). Small tortuous tubes are prevalent inside the gels (FIG. 3C).
Figure 3B:
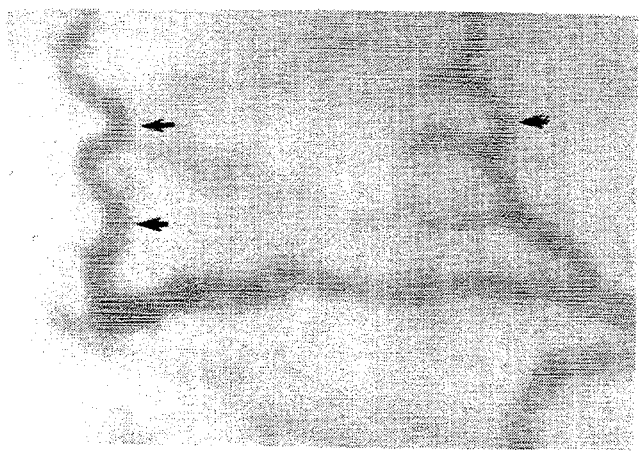
Figure 3C:
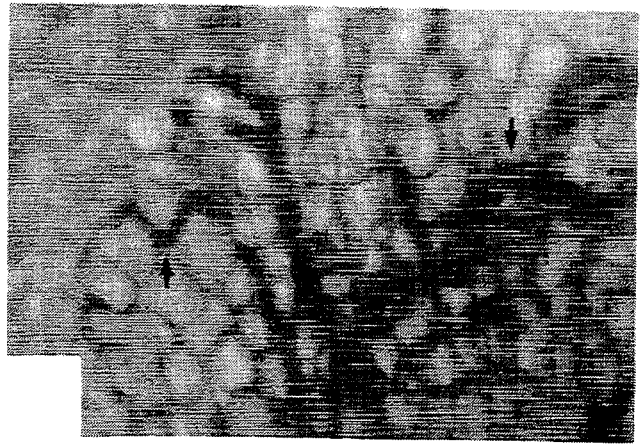
Figure 5A:
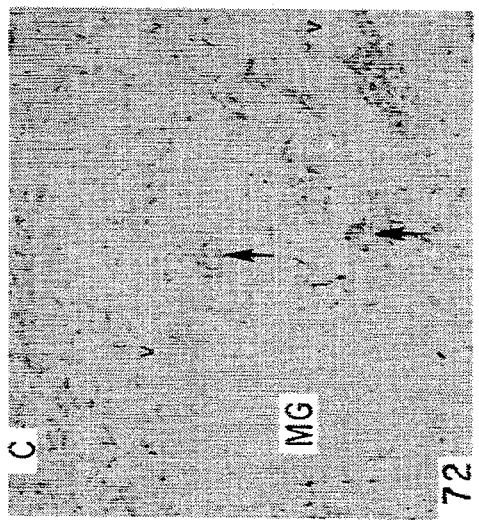
FIGS. 5-5D are a factor VIII staining of neovessels.
Figure 5B:
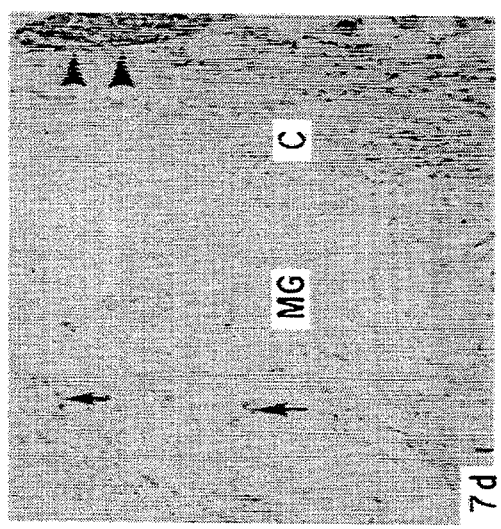
Figure 5C:
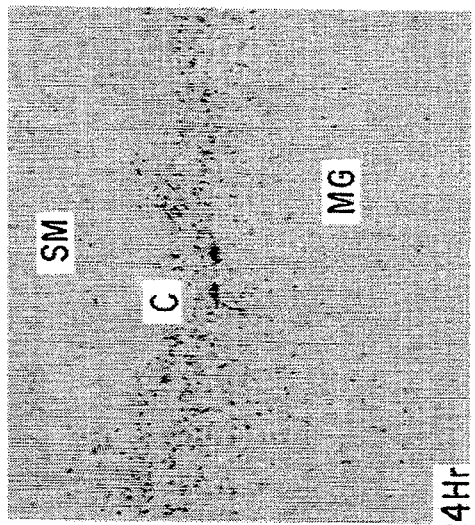
Figure 5D:
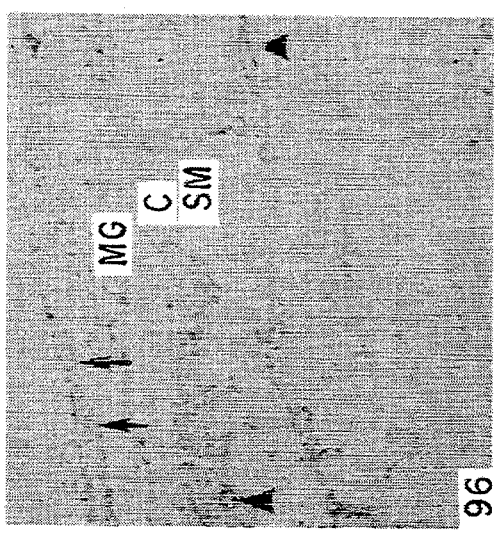

FIGS. 3A–3C are photographs of vessels associated with the FGF/heparin-supplemented gels. Vessels surrounding the gel appear to derive from the skin and peritoneal linings (FIGS. 3A and 3B). Small tortuous tubes are prevalent inside the gels (FIG. C). The effect of the age of the animal on the angiogenic response showed that vessel formation was reduced in young (6 month) animals compared to older mice (12, 18, or 24 months of age) where the response was typically twice as strong.

FIG. 4 is the histological analysis of recovered gels showing time course of vessel formation. Samples were prepared for histology as described below at different times after injection of MATRIGEL containing FGF and heparin. The Trichrome-Masson stained specimens show the progressive invasion of cells into the MATRIGEL (MG) over 6, 24, 48 and 96 hours (top 4 panels: Mag=125×). By 7 days, there is more organization of the cells into linear structures. At higher magnification (500×; middle panel, 7 day), the connective septa within the MATRIGEL exhibits large blood vessels from which an extension of a vessel into the MATRIGEL is evident (two arrows). At 8 days, many of the vessels within the MATRIGEL are well formed exhibiting a clear endothelium (End).

Sections examined with the Trichrome-Masson stain (FIG. 4) showed that cells invaded the gel within 24 hours and persisted for up to 8 days with a progressive increase in linear structures containing red blood cells indicative of functional vessels. Sections of the gel were reacted with antibody to factor VIII antigen (von Willebrand factor) to confirm the presence of endothelial cells in association with the vessels.

FIG. 5 is a factor VIII staining of neovessels. Gels recovered after 1, 3, 4 and 7 days, were stained with von Willebrand factor antibody as described below. The presence of neovessels (arrows) in the MATRIGEL (MG) layer can be distinguished from existing vessels (arrowheads) near the skeletal muscle (SM) and collagen (C) interface. Small vessels (72 hours), horizontally coursing structures (96 hours), and ramifying blood vessels (7 days) are noted. Vacuoles (v); Magnification ×40. The presence of capillary-sized vessels in the gel was apparent at 72 hours (FIG. 5). These neovessels were also apparent by 48 hours (not shown) and are smaller than other factor VIII positive structures (pre-existing vessels) on the periphery of the Matrigel (FIG. 5, arrowheads). Neovascularization was not observed at 24 hours although inflammatory cells were observed in the region between the Matrigel and skeletal muscle.

Figure 6A:
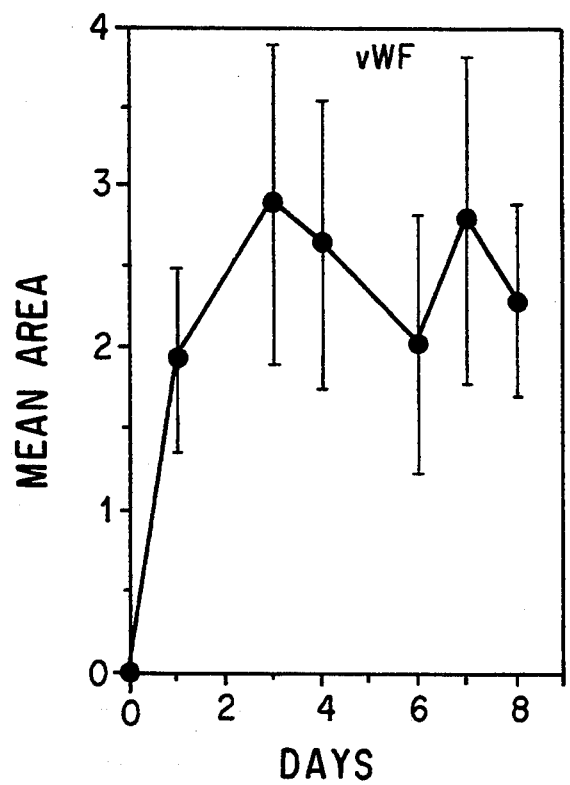
FIGS. 6A and 6B are quantitations of neovascularization.
Figure 6B:
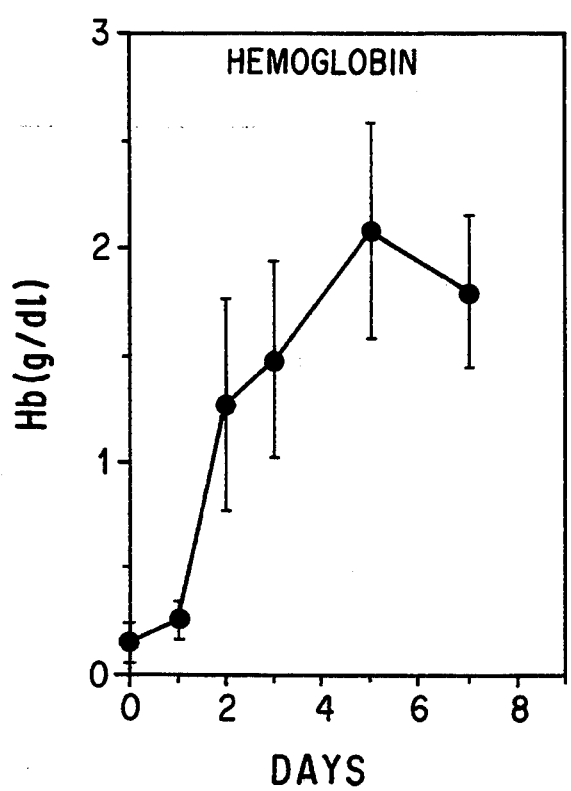

FIGS. 6A and 6B are quantitations of neovascularization. Histological slides were examined with an Optomax image analysis system and the mean area in a 20× or 40× field was quantitated for slides stained with von Willebrand factor antibody (vWF). Each point represents the mean area per field ($\times 10^5 \mu m^2$) of 10–20 fields and error bars are for standard deviation from the mean. Hemoglobin measurements (g/dl) at these time points were determined as described below and in Table 1. The data represent the mean hemoglobin values from at least 5 mice per point with standard errors of the mean as indicated. The increase in vessels in the gels, based on specific von Willebrand factor (vWF) stain as quantitated by an image analysis system (FIG. 6, vWF), was similar to the increase in cells (hematoxylin/eosin and Trichrome stain, not shown). Measurement of hemoglobin content indicated formation of a functional vasculature at the site of anglogenesis. As judged by hemoglobin content, the angiogenic response to FGF was time dependent, clearly visible by day 1–2, reached a plateau by day 3–4, and persisted through day 8 (FIG. 6, Hemoglobin) occurring with similar kinetics as observed for the accumulation of neovessels (FIG. 6, vWF).

In the presence of heparin (64 U/ml), the maximal angiogenic response occurred at 1 ng/ml of aFGF (Table 1) followed by a decrease and then a subsequent increase at higher levels of FGF. These data are consistent with the down-regulation of FGF receptors in the presence of higher levels of the growth factor. In some experiments, higher doses of FGF were used (125 and 250 ng FGF/ml) and these showed responses similar to those observed at 100 ng/ml. In contrast, heparin induced a linear increase in angiogenesis in the presence of 1 ng/ml FGF (Table 1). The lowest concentration of heparin that resulted in consistent vascularization of the gels was 40 U/ml. At this concentration of heparin, the FGF response was also biphasic with an optimum again at 1 ng/ml (data shown). The amount of aFGF (0.5 ng) required for an angiogenic response in these assays is similar to the levels of FGF necessary for endothelial cell growth in culture and to the levels required to elicit an angiogenic response in the chick allantoic membrane. The results suggest that the angiogenic response induced by heparin and aFGF occurs at physiologically relevant doses of FGF observed previously using other assays and other angiogenic factors.

TABLE I

Acidic FGF Demonstrates a Biphasic Angiogenic Response Which is Enhanced by Heparin

| aFGF (ng/ml)[a] | Hb (g/dl)[b] |
| --- | --- |
| 0 | 0.28 (±0.36) |
| 0.1 | 1.00 (±0.45) |
| 1.0 | 3.20 (±2.20) |
| 10 | 0.23 (±0.15) |
| 100 | 0.94 (±1.18) |

| Heparin (U/ml)[c] | Hb (g/dl) |
| --- | --- |
| 2.0 | — |
| 6.0 | 0.04 (±0.03) |
| 20 | 0.15 (±0.20) |
| 32 | 0.16 (±0.49) |
| 40[d] | 0.69 (±0.60) |
| 64 | 2.72 (±1.00) |

[a]MATRIGEL gels contained 64 U heparin/ml and were processed 3 days after injection.
[b]Hemoglobin values (mean ± sem) represent the average of at least 5 animals.
[c]MATRIGEL contained FGF at 1 ng/ml for each experiment.
[d]Heparin at 40 U/ml was the lowest concentration to yield consistent vessel formation.

EXAMPLE 2

In this example, several cytokines were tested for angiogenic activity in the presence of heparin to determine whether the assay was comparable to other established angiogenesis. The assays results are listed in Table 2 below. Of the various factors tested, aFGF, bFGF, and TNF-α induced an angiogenic response (Table 2), consistent with previous reports on these factors whereas TGFβ, PDGF, IL-1, and IL-6 were inactive.

TABLE 2

Detection of Angiogenic Activity Using Various Neovascularization Factors

| Factors added to Matrigel + Heparin[a] | Hb (g/dl) |
| --- | --- |
| — | 0.10 (±0.02) |
| 1 ng/ml aFGF | 1.30 (±0.07)[b] |
| 20 ng/ml TGFβ | 0.06 (±0.02) |
| 2 ng/ml PDGF BB | 0.10 (±0.06) |

TABLE 2-continued

Detection of Angiogenic Activity Using Various Neovascularization Factors

| Factors added to Matrigel + Heparin[a] | Hb (g/dl) |
| --- | --- |
| 20 ng/ml PDGF BB | 0.15 (±0.08) |
| 200 ng/ml PDGF BB | 0.07 (±0.03) |
| 5 U/ml PDGF AB | 0.11 (±0.04) |
| 1 ng/ml 1IL-1β | 0.22 (±0.02) |
| 10 ng/ml IL-6 | 0.18 (±0.05) |
| 1.0 ng/ml BFGF | 0.14 (±0.13) |
| 10 ng/ml BFGF | 0.20 (±0.17) |
| 100 ng/ml BFGF | 0.86 (±0.70)[b] |
| 10 ng/ml TNFα | 2.30 (±2.00)[b] |

[a]MATRIGEL (0.5 ml) and heparin (40 U/ml) were mixed with various factors and injected subcutaneously. Responses were quantitated 4 days later. TGF-β, PDGF BB, IL-6, IL-1βor PDGF AB did not induced neovascularization.
[b]Acidic FGF, basic PGF, or TNF-β were potent induces of angiogenesis.

EXAMPLE 3

In this example, the angiostatic activity of certain cyrokines when aFGF was included were assessed. The results of these assays are given in Table 3 below. Interleukin 1β, interleukin-6, and TGFβ inhibited the angiogenic response to aFGF. The TGFβ dose response showed inhibition at concentrations as low as 0.2 ng/ml. PDGF BB was also a potent inhibitor probably acting indirectly since endothelial cells do not express a receptor for this factor.

TABLE 3

| Factors added to MATRIGEL + Heparin + aFGF[a] | Hb (g/dl) |
| --- | --- |
| — | 1.30 (±0.07) |
| 10 ng/ml TNFα | 1.10 (±1.10) |
| 0.02 ng/ml TGFβ | 1.70 (±1.50) |
| 0.2 ng/ml TGFβ | 0.08 (±0.05) |
| 2.0 ng/ml TGFβ | 0.15 (±0.13) |
| 20 ng/ml TGFβ | 0.24 (±0.25) |
| 200 ng/ml PDGF BB | 0.16 (±0.07) |
| 1 ng/ml IL-1β | 0.14 (±0.10) |
| 10 ng/ml IL-6 | 0.17 (±0.12) |

[a]Gels contained aFGF (1 ng/ml) + heparin (40 U/ml) and various cytokines. Hemoglobin levels in the gels are shown after 4 days. Tumor necrosis factor β and TGF-β had no effect on the angiogenic response. PDGF BB, IL-1β, IL-6, and TGF-β inhibited the response.

The tissue inhibitor of metalloproteinases (TIMP), a collagenase inhibitor, is also found in cartilage where it may maintain cartilaginous tissue in an avascular state by inhibiting endothelial cell migration. FIG. 7 is a bar graph showing inhibition by TIMP. Tissue inhibitor of metalloproteinases (collagenase inhibitor) is a potent inhibitor of aFGF-induced angiogenesis. Recombinant TIMP protein (0.5 mg/ml) was included with MATRIGEL (0.5 ml), FGF (1 ng/ml), and heparin (64 U/ml) at the time of injection (hatched bars). Gels from at least 5 animals per point were analyzed after day 1 or day 3. Shown for comparison are the hemoglobin levels in gels that contained MATRIGEL, FGF, and heparin, but lacking TIMP (solid bars).

Addition of recombinant TIMP at 0.5 mg/ml in the MATRIGEL/heparin/FGF mixtures showed essentially complete inhibition of neovascularization at day 3 as measured both by hemoglobin content (FIG. 7) and by examination of the gel for infiltrating vessels (not shown). These observations are consistent with the known role of metalloproteases in the invasion of endothelial cells through basement membrane and for the role of metalloproteases in angiogenesis.

In some experiments, the gels supplemented with FGF and heparin were removed after 4 days in vivo and dissociated with collagenase/dispase. The cells isolated from the gels were cultured and probed with antibody for von-Willebrand factor. These studies suggested that cells isolated and cultured from the vascularized gels were positive for vWf and thus were endothelial cells. Also, when these cells were plated onto the surface of MATRIGEL, they were found to form capillary-like tubes (data not shown) as observed previously for human umbilical vein endothelial cells. Cells could be isolated from vascularized gels taken from both young and old animals.

For histology and factor VIII and related antigen staining as discussed above all specimens were fixed in 10% buffered formalin for at least 24 hours, progressively dehydrated in increasing percentages of ethyl alcohol (70, 80, 95, 100, 100, 100%) cleared in Histoclear, embedded in paraffin under vacuum, sectioned at 5 micron thickness, deparaffinized, and stained with Harris hematoxylin and eosin.

Selected specimens were also stained for Factor VIII-related antigen using an immunoperoxidase method described by Cartrun et al, "An Immunocytochemical Technique Offering Increased Sensitivity and Lowered Cost with a Streptavidin-Horseradish Peroxidase Conjugate", *The Journal of Histotechnology*, Vol. 12 (1989), pages 273-277, the disclosure of which are expressly incorporated herein by reference or Trichrome-Masson. Briefly, 5 micron sections were placed on silanized slides, dried overnight at 64° C., deparaffinized, hydrated, a placed into 3% hydrogen peroxide to quench endogenous peroxide. After rinsing in deionized water, the slides were enzymatically treated with 0.05% Pronase (Calbiochem, San Diego, Calif.) in phosphate buffered saline (PBS) with 0.114% ethylenediaminetetraacitic acid at 37° C. for 20 minutes. Enzyme activity was then abolished with 95% ethanol for 5 minutes. After PBS rinsing, rabbit anti-human von Willebrand Factor antibody (Dako, Carpinteria, Calif.) diluted 1:1000 in 0.05% non-fat dry milk (NFDM) in PBS was applied to the slides which were placed in a humidity chamber overnight at 4° C. After rinsing in PBS the next morning, the test slides were incubated at room temperature for 20 minutes in biotinylated anti-rabbit IgG (Vector, Burlingame, Calif.) diluted 1:1000 in PBS with 0.5% NFDM. Nonimmune goat serum (5% v/v) was added to block nonspecific staining. The slides were then rinsed in three changes of PBS, incubated for 20 minutes in horseradish peroxidase conjugated streptavidin (Jackson ImmunoResearch, West Grove, Pa.), diluted 1:1500 in PBS with 0.5% NFDM, rinsed in tap water, dried, mounted in Crystal Mount, dried at 80° C. for 20 minutes, and coverslipped with Permount.

For isolation of ebdothelial cells from the angiogenic cells as discussed above dissected gels were placed in sterile tissue culture dishes and the skin and peritoneal lining were trimmed with scalpels. The Matrigel was dispersed by passing through a 19 g needle in endothelial cell culture media: Medium 199 containing 20% fetal bovine serum, 100 μg/ml endothelial cell growth supplement (Biomedical Technologies, Inc.), 16 U/ml heparin, antibiotics and non-essential amino acids. The gel pieces were concentrated by centrifugation (1000 rpm, 10 min) in a Beckman GPR centrifuge, resuspended in endothelial cell culture medium, and cultured overnight in the same medium and gel pieces were centrifuged to remove medium and the gel pieces were treated at 37° C. with 1 mg/ml collagenase/dispase (Boehringer/Mannhein #269638) in culture medium for 20 minutes. The gel pieces were concentrated by centrifugation and re-cultured in endothelial cell medium. The culture plates were washed the next day and the gel pieces were transferred to another set of culture plates. Surviving cells were sub-cultured and assayed for von Willebrand antigen.

During the course of the present invention a quantitative angiogenesis assay based on the ability of an extract of basement membrane proteins (MATRIGEL) to form a solid gel when injected into mice and to support a rapid and intense angiogenic reaction in the presence of FGF and heparin has been developed. It has been discovered that MATRIGEL, while stimulating cell attachment and morphogenesis when used as a substratum in tissue culture, does not induce an angiogenic response in vivo by itself. MATRIGEL has further been found to promote the differentiation of endothelial cells into capillary-like structures in culture and when used as a vehicle in vivo may enhance the selectivity of endothelial cells entering the gel since basement membranes are not readily crossed by fibroblasts and certain other cells.

Gels supplemented with FGF and heparin induced intense vascularization. Numerous large vessels were apparent on the surface of the gel while the vessels within the gel were smaller and more tortuous. Vessel formation was quantitated by measuring the hemoglobin present in the dissected gels and confirmed by histological staining for yon Willebrand factor and by the isolation of factor VIII positive cells from the gel. Vessel formation was apparent as early as 2 days, reached a plateau after 4 days, and persisted up to 8 days. Maximal and consistent responses required both FGF and heparin and distinct concentrations of each factor were required for optimal responses. The site of injection and the age of the animal affected the magnitude of the response.

The correlation of hemoglobin content with vessel formation was previously described using alginate-entrapped tumor cells to elicit angiogenesis in vivo. Factor VIII-stainable vessels were found to correlate with hemoglobin content and pooling of radiolabeled red blood cells at the alginate injection site. The requirement for heparin with FGF in angiogenesis assays and fibroblast growth and differentiation appears to be due to both a stabilization of FGF and conformational changes in FGF required for receptor binding. Heparin also enhances the angiogenic activity of factors produced by 3T3 adipocytes, recently shown to be mediated by monobutyrin. The tests conducted during the course of the present invention shown that aFGF was potent at concentrations reported previously to be effective in both in vivo and in vitro assays. The time course of the response was also comparable to results obtained with FGF in other assays and similar to that reported for other angiogenic agents like antiotropin. Not unexpectedly, the antiogenic response to FGF occurred more rapidly than the response observed with anginate-encapsulated tumor cells which presumably require some time to generate their own factor(s). A related angiogenic factor, vascular permeability factor, has been shown to induce vascular permeability in vivo at 8 ng per animal and is active between 0.1 ng/ml and 2 ng/ml as a mitogen for endothelial cells in vitro. In addition, the vascular permeability factor induces angiogenesis in the rat corneal assay at a dose of 20 ng. An unrelated chemical inducer of angiogenesis, monobutyrin, has been shown to be antiogenic in the CAM assay at 20 pg (0.14 pmole) while aFGF in the present assays is active at 0.025 pmole.

Other cytokines were tested in this assay including IL-1$\beta$, IL-6, and TGF-$\beta$ and these were found to be potent inhibitors. IL-6 enhances the production of TIMP which may inhibit collagenase and endothelial cell migration. TGF-$\beta$ inhibits endothelial cell proliferation and migration, although it does exhibit angiogenesis in vivo in some assays. IL-1 has been shown to regulate endothelial cell growth via autocrine mechanisms which may lead to programmed cell death (apoptosis) as is observed in endothelial cells deprived of FGF. TNF-$\alpha$ and bFGF induced neovessel formation. TNF$\alpha$ has been shown to activate macrophages which in turn produce angiogenic factors.

In summary, the advantages of the assay of the present invention are that it is rapid, reproducible, quantitative, and does not require a surgical procedure for implantation. It allows the detection of both angiogenic and anti-angiogenic factors and endothelial cells penetrating the gel can be isolated as discussed above for further study. This system has also been used to assess the capacity of mice of different ages to initiate an antiogenic response and this type of study would be of interest in both hypertensive and diabetic mice. Such systems may be used in identifying and isolating biological factors and drugs able to regulate angiogenesis. In addition, the procedure will allow for inducement of an additional vascular supply in wounded or ischemic tissue where it is needed to restore normal healing and regeneration. Finally, the procedure can be used to inhibit or suppress vascularization at the situs of augmented angiogenesis, such as tumor growth.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims that follow.

What is claimed is:

1. A method of performing an in vivo angiogenesis assay which comprises:
   providing a liquid matrix material which forms a matrix gel when injected into a host wherein said liquid matrix material is MATRIGEL;
   adding an angiogenesis inducing or inhibiting agent to said liquid matrix material;
   injecting said liquid matrix material containing said angiogenesis inducing or inhibiting agent into a host to form a matrix gel;
   recovering said matrix gel from said host; and
   quantitating angiogenesis of said recovered matrix gel.

2. A method of performing an in vivo angiogenesis assay according to claim 1 wherein said angiogenesis quantitating includes quantitating vessel formation.

3. A method of performing an in vivo angiogenesis assay according to claim 2 wherein said angiogenesis quantitating includes determining hemoglobin content.

4. A method of performing an in vivo angiogenesis assay according to claim 1 wherein said angiogenesis quantitating includes isolating endothelial cells which penetrate said gel matrix.

5. A method of performing an in vivo angiogenesis assay according to claim 1, wherein said angiogenesis inducing agent is selected from the group consisting of fibroblast growth factor (FGF), heparin and mixtures thereof.

6. A method of inducing vascularization in a tissue situs which comprises:
   providing a liquid matrix material which forms a matrix gel when injected into a host wherein said liquid matrix material is MATRIGEL;
   adding an angiogenic inducing agent to said liquid matrix material; and
   injecting said liquid matrix material containing said angiogenic inducing agent into a tissue situs of a host to form a matrix gel.

7. A method of inducing vascularization in a tissue situs according to claim 6, wherein said tissue situs comprises a wound.

8. A method of inducing vascularization in a tissue situs according to claim 6, wherein said tissue situs comprises an area of ischemic tissue.

9. A method of inhibiting vascularization in a tissue situs which comprises:
   providing a liquid matrix material which forms a matrix gel when injected into a host wherein said liquid matrix material is MATRIGEL;
   adding an angiogenic inhibiting agent to said liquid matrix material; and
   injecting said liquid matrix material containing said angiogenic inhibiting agent into a tissue situs of a host to form a matrix gel.

10. A method of inhibiting vascularization in a tissue situs according to claim 9, wherein said tissue situs comprises a site of augmented angiogenesis.

* * * * *